United States Patent
Weber et al.

(10) Patent No.: US 12,171,552 B2
(45) Date of Patent: *Dec. 24, 2024

(54) METHOD AND APPARATUS FOR CALIBRATION TO REDUCE COUPLING BETWEEN SIGNALS IN A MEASUREMENT SYSTEM

(71) Applicant: Masimo Corporation, Irvine, CA (US)

(72) Inventors: Walter M. Weber, Laguna Hills, CA (US); Ammar Al-Ali, San Juan Capistrano, CA (US); Mohamed K. Diab, Ladera Ranch, CA (US); Marcelo M. Lamego, Cupertino, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,187

(22) Filed: Apr. 28, 2023

(65) Prior Publication Data
US 2023/0346270 A1    Nov. 2, 2023

Related U.S. Application Data

(63) Continuation of application No. 16/993,101, filed on Aug. 13, 2020, now Pat. No. 11,672,447, which is a continuation of application No. 15/834,965, filed on Dec. 7, 2017, now Pat. No. 10,772,542, which is a continuation of application No. 14/836,635, filed on Aug. 26, 2015, now Pat. No. 9,861,305, which is a continuation of application No. 13/526,376, filed on
(Continued)

(51) Int. Cl.
A61B 5/1455   (2006.01)
A61B 5/00     (2006.01)
A61B 5/1495   (2006.01)

(52) U.S. Cl.
CPC .......... *A61B 5/1455* (2013.01); *A61B 5/1495* (2013.01); *A61B 5/7228* (2013.01); *A61B 2562/0238* (2013.01)

(58) Field of Classification Search
CPC . A61B 5/0205; A61B 5/1455; A61B 5/14551; A61B 5/14552; A61B 5/1495; A61B 5/7228; A61B 2562/0233; A61B 2562/0238
See application file for complete search history.

(56) References Cited

U.S. PATENT DOCUMENTS

| | | |
|---|---|---|
| 4,942,877 A | 7/1990 | Sakai et al. |
| 4,960,128 A | 10/1990 | Gordon et al. |

(Continued)

OTHER PUBLICATIONS

US 2022/0192529 A1, 06/2022, Al-Ali et al. (withdrawn)
US 2024/0016391 A1, 01/2024, Lapotko et al. (withdrawn)

*Primary Examiner* — Chu Chuan Liu
(74) *Attorney, Agent, or Firm* — Knobbe, Martens, Olson & Bear, LLP

(57) ABSTRACT

A method and an apparatus for separating a composite signal into a plurality of signals is described. A signal processor receives a composite signal and separates a composite signal into separate output signals. Feedback from one or more of the output signals is provided to a configuration module that configures the signal processor to improve a quality of the output signals. In one embodiment, calibration data from multiple calibration data sets is used to configure the demodulation of the composite signal into separate output signals.

5 Claims, 4 Drawing Sheets

Related U.S. Application Data

Jun. 18, 2012, now abandoned, which is a continuation of application No. 11/871,636, filed on Oct. 12, 2007, now abandoned.

(60) Provisional application No. 60/851,112, filed on Oct. 12, 2006.

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,460,182 A | 10/1995 | Goodman et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,774,213 A | 6/1998 | Trebino et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Ai-Ali |
| 6,678,543 B2 | 1/2004 | Diab et al. |

(56) References Cited

U.S. PATENT DOCUMENTS

| | | |
|---|---|---|
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Ai-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Ai-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |

(56) References Cited

U.S. PATENT DOCUMENTS

| | | |
|---|---|---|
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |

(56) References Cited

U.S. PATENT DOCUMENTS

| | | |
|---|---|---|
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |

(56) References Cited

U.S. PATENT DOCUMENTS

| | | |
|---|---|---|
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Ai-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B2 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |

(56) References Cited

U.S. PATENT DOCUMENTS

| | | |
|---|---|---|
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali et al. |
| 10,471,159 B1 | 11/2019 | Lapotko et al. |
| 10,478,107 B2 | 11/2019 | Kiani et al. |
| 10,503,379 B2 | 12/2019 | Al-Ali et al. |
| 10,505,311 B2 | 12/2019 | Al-Ali et al. |
| 10,512,436 B2 | 12/2019 | Muhsin et al. |
| 10,524,706 B2 | 1/2020 | Telfort et al. |
| 10,524,738 B2 | 1/2020 | Olsen |
| 10,531,811 B2 | 1/2020 | Al-Ali et al. |
| 10,531,819 B2 | 1/2020 | Diab et al. |
| 10,531,835 B2 | 1/2020 | Al-Ali et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,548,561 B2 | 2/2020 | Telfort et al. |
| 10,555,678 B2 | 2/2020 | Dalvi et al. |
| 10,568,514 B2 | 2/2020 | Wojtczuk et al. |
| 10,568,553 B2 | 2/2020 | O'Neil et al. |
| RE47,882 E | 3/2020 | Al-Ali |
| 10,575,779 B2 | 3/2020 | Poeze et al. |
| 10,582,886 B2 | 3/2020 | Poeze et al. |
| 10,588,518 B2 | 3/2020 | Kiani |
| 10,588,553 B2 | 3/2020 | Poeze et al. |
| 10,588,554 B2 | 3/2020 | Poeze et al. |
| 10,588,556 B2 | 3/2020 | Kiani et al. |
| 10,595,747 B2 | 3/2020 | Al-Ali et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,772,542 B2 | 9/2020 | Weber et al. |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,672,447 B2 | 6/2023 | Weber et al. |
| 11,678,829 B2 | 6/2023 | Al-Ali et al. |
| 11,679,579 B2 | 6/2023 | Ai-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |

(56) References Cited

U.S. PATENT DOCUMENTS

| | | |
|---|---|---|
| D1,036,293 S | 7/2024 | Al-Ali et al. |
| 12,029,844 B2 | 7/2024 | Pauley et al. |
| 12,048,534 B2 | 7/2024 | Vo et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0010092 A1 | 1/2005 | Weber et al. |
| 2005/0030884 A1 | 2/2005 | Kim et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Ai-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2011/0237969 A1 | 9/2011 | Eckerbom et al. |
| 2012/0046557 A1 | 2/2012 | Kiani |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081100 A1 | 3/2014 | Muhsin et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0336481 A1 | 11/2014 | Shakespeare et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366507 A1 | 12/2015 | Blank et al. |
| 2015/0380875 A1 | 12/2015 | Coverston et al. |
| 2016/0029932 A1 | 2/2016 | Ai-Ai |
| 2016/0051205 A1 | 2/2016 | Al-Ali et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |

(56) References Cited

U.S. PATENT DOCUMENTS

| | | |
|---|---|---|
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0332976 A1 | 11/2017 | Al-Ali |
| 2018/0069776 A1 | 3/2018 | Lamego et al. |
| 2018/0103874 A1 | 4/2018 | Lee et al. |
| 2018/0110478 A1 | 4/2018 | Al-Ali |
| 2018/0116575 A1 | 5/2018 | Perea et al. |
| 2018/0130325 A1 | 5/2018 | Kiani et al. |
| 2018/0161499 A1 | 6/2018 | Al-Ali et al. |
| 2018/0174679 A1 | 6/2018 | Sampath et al. |
| 2018/0174680 A1 | 6/2018 | Sampath et al. |
| 2018/0192955 A1 | 7/2018 | Al-Ali et al. |
| 2018/0214031 A1 | 8/2018 | Kiani et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0256113 A1 | 9/2018 | Weber et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0021638 A1 | 1/2019 | Al-Ali et al. |
| 2019/0090748 A1 | 3/2019 | Al-Ali |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Ai-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |

(56) References Cited

U.S. PATENT DOCUMENTS

| | | |
|---|---|---|
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |

METHOD AND APPARATUS FOR CALIBRATION TO REDUCE COUPLING BETWEEN SIGNALS IN A MEASUREMENT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application is a continuation of U.S. application Ser. No. 16/993,101, filed Aug. 13, 2020, titled METHOD AND APPARATUS FOR CALIBRATION TO REDUCE COUPLING BETWEEN SIGNALS IN A MEASUREMENT SYSTEM, now U.S. U.S. Pat. No. 11,672,447, which is a continuation of U.S. application Ser. No. 15/834,965, filed Dec. 7, 2017, titled METHOD AND APPARATUS FOR CALIBRATION TO REDUCE COUPLING BETWEEN SIGNALS IN A MEASUREMENT SYSTEM, now U.S. Pat. No. 10,772,542, which a continuation of U.S. application Ser. No. 14/836,635, filed Aug. 26, 2015, titled "METHOD AND APPARATUS FOR CALIBRATION TO REDUCE COUPLING BETWEEN SIGNALS IN A MEASUREMENT SYSTEM," now U.S. Pat. No. 9,861,305, which is a continuation of U.S. application Ser. No. 13/526,376, filed Jun. 18, 2012, titled "METHOD AND APPARATUS FOR CALIBRATION TO REDUCE COUPLING BETWEEN SIGNALS IN A MEASUREMENT SYSTEM," which is a continuation of U.S. patent application Ser. No. 11/871,636, filed Oct. 12, 2007, titled "METHOD AND APPARATUS FOR CALIBRATION TO REDUCE COUPLING BETWEEN SIGNALS IN A MEASUREMENT SYSTEM", which claims priority benefit of U.S. Provisional Application No. 60/851,112, filed Oct. 12, 2006, titled "METHOD AND APPARATUS FOR CALIBRATION TO REDUCE COUPLING BETWEEN SIGNALS IN A MEASUREMENT SYSTEM", the entire contents of which is hereby incorporated by reference.

BACKGROUND

Field of the Disclosure

The present invention relates to the field of signal processing, and more particularly, relates to multi-channel demodulators for demodulating mixed signals, such as, for example, signals generated in a pulse oximetry system.

Background

In many multi-channel measurement and communication systems, crosstalk between channels and corruption of data within the channels are significant problems. Such problems can arise from variations in manufacturing tolerances, movement, propagation delays, phase shifts, temperature effects, degradation of components due to age or other factors, noise, etc.

A pulse oximetry system is one example of a system where the above-referenced problems are found. In a pulse oximetry system, blood oxygen saturation is determined by transmitting pulses of electromagnetic energy through a portion of a subject having blood flowing therein (e.g., through a finger, through an ear lobe, or other portion of the body where blood flows close to the skin). The pulses of electromagnetic energy comprise periodic pulses of red light having wavelengths of approximately 660 nanometers, for example, and periodic pulses of infrared light having wavelengths of approximately 905 nanometers.

After propagating through the portion of the subject, the red pulses and the infrared pulses are detected by a detector which is responsive to light at both wavelengths and which generates an electrical signal that has a relationship to the intensity of the electromagnetic energy incident on the detector. The detector output is a two-channel signal having a first signal component corresponding to the detected red pulses and a second signal component corresponding to the detected infrared pulses.

The two-channel signal is demodulated to recover separate signals corresponding to the first signal component and the second signal component. However, prior art demodulators are not sufficiently accurate enough to completely separate the two signal components in all cases. Thus, it is not uncommon for the first demodulator output signal (corresponding to the first signal component) to contain residual components of the second signal and vice versa. This crosstalk between the first and second signal components reduces the accuracy of the recovered first and second signals. In multi-channel systems with more than two channels, crosstalk can occur between all of the channels, again reducing accuracy.

SUMMARY

The present invention solves these and other problems by separating a combined multi-channel signal into a plurality of output signals in a manner that reduces crosstalk and other contamination in the plurality of output signals. In one embodiment, the separator includes a multi-channel demodulator that is first configured using nominal values for the various components in the signal path. In one embodiment, the multi-channel demodulator is further configured using data obtained from calibration measurements. In one embodiment, the calibration measurements are made during an initialization period. In one embodiment, the calibration measurements are made frequently, continuously, or at selected intervals. In one embodiment, calibrations are performed on at least one of, initialization, on command, on attachment of a new sensor, continuously, and/or interspersed with measurements. In one embodiment of a system for measuring one or more blood constituents, the calibration measurements are made when the system detects that a patient has been connected to the system. In one embodiment, the multi-channel demodulator is further configured at regular intervals by re-running the calibration measurements. In one embodiment, the multi-channel demodulator comprises an optimizing demodulator. In one embodiment, crosstalk in the multi-channel demodulator is reduced by computing an amplitude and/or phase adjustment of one or more demodulation signals that are provided respectively to one or more mixers.

In one embodiment, an apparatus for measuring blood oxygenation in a subject includes a first signal source which applies a first input signal during a first time interval. A second signal source applies a second input signal during a second time interval. A detector detects a first parametric signal responsive to the first input signal passing through a portion of the subject having blood therein and detects a second parametric signal responsive to the second input signal passing through the portion of the subject. The detector generates a detector output signal responsive to the first and second parametric signals. A signal processor receives the detector output signal and demodulates the detector output signal by applying a first demodulation signal to a signal responsive to the detector output signal to generate a first demodulator output signal and applying a second demodulation signal to the signal responsive to the detector output signal to generate a second demodulator output signal. In one embodiment, the first demodulation signal has at least one component comprising a first frequency, a first phase, and a first amplitude; and the second demodulation signal has at least one component comprising a second frequency, a second phase, and a second amplitude. In one embodiment, the first phase and the second phase are chosen to reduce crosstalk from the first parametric signal to the second demodulator output signal and to reduce crosstalk from the second parametric signal to the first demodulator output signal. In one embodiment, the first amplitude and the second amplitude are chosen to reduce crosstalk from the first parametric signal to the second demodulator output signal and to reduce crosstalk from the second parametric signal to the first demodulator output signal. In one embodiment, at least one of the first amplitude, the first phase, the second amplitude, and the second phase are chosen to reduce crosstalk from the first parametric signal to the second demodulator output signal and to reduce crosstalk from the second parametric signal to the first demodulator output signal.

In one embodiment, at least one of the first amplitude, the first phase, the second amplitude, and the second phase is determined by turning off one of the first and second signal sources and measuring the crosstalk between one of the parametric signals and the non-corresponding output signal.

One embodiment includes a method of reducing crosstalk between two signals generated by applying a first pulse and a second pulse to measure a parameter. The first pulse and the second pulse are applied periodically at a repetition rate defining a period. The first pulse is generated during a first interval in each period and the second pulse is generated during a second interval in each period. In one embodiment, the second interval is spaced apart from the first interval. In one embodiment, the second interval overlaps at least a portion of the first interval. The first and second pulses produce first and second parametric signals responsive to the parameter. The first and second parametric signals are received by a detector which outputs a composite signal responsive to the first and second parametric signals. The method includes applying a first demodulation signal to the composite signal to generate a first demodulated output signal. The first demodulation signal includes at least one component having at least a first amplitude and a first phase. The method further includes applying a second demodulation signal to the composite signal to generate a second demodulated output signal. The second demodulation signal includes at least one component having at least a second amplitude and a second phase. The method further includes lowpass filtering the first demodulated output signal to generate a first recovered output signal responsive to the first parametric signal, and lowpass filtering the second demodulated output signal to generate a second recovered output signal responsive to the second parametric signal. The method also includes choosing at least one of the first phase, the first amplitude, the second phase, and the second amplitude to reduce crosstalk components in the first recovered output signal and the second recovered output signal. In one embodiment, the method also includes choosing the first phase and/or the second phase to reduce crosstalk components in the first recovered output signal and the second recovered output signal.

In one embodiment, the first phase and the second phase are chosen by applying a first light pulse pattern (activation pattern) during a first time period and measuring the first recovered output during the first time period as a first calibration output, and measuring the second recovered output during the first time period as a second calibration output. The method includes applying a second light pulse activation pattern during a second time period and measuring the first recovered output during the first time period as a third calibration output and measuring the second recovered output during the second time period as a fourth calibration output. The method further includes computing the first phase and the second phase from at least the first calibration output, the second calibration output, the third calibration output, and the fourth calibration output.

In one embodiment, the first phase is computed from a ratio of the first calibration output and the second calibration output.

In one embodiment, the first demodulation signal includes a sum of a first demodulation component having a first amplitude and a second demodulation component having a second amplitude. The second demodulation component is in quadrature with the first demodulation component and the act of choosing the first phase involves choosing the first amplitude and the second amplitude. In one embodiment, the quadrature components are sinusoidal and cosinusoidal.

In one embodiment, the first demodulation signal includes a sum of a sinusoidal component having a first amplitude and a cosinusoidal component having a second amplitude. The first amplitude and the second amplitude are chosen by a least squares minimization of an error corresponding to the crosstalk. In one embodiment, the error is integrated over a time period corresponding to an integer number of cycles of the sinusoidal component.

In one embodiment, a first demodulation signal is applied to a composite signal having first and second coefficients to generate a first demodulated signal. The first demodulation signal includes a first component having a first amplitude and a second component having a second amplitude. The first and second components being in quadrature. The second amplitude has a predetermined relationship to the first amplitude. The predetermined relationship is selected to cause the first demodulated signal to have lower frequency components that include a primary component corresponding primarily to the first desired component and a residual component corresponding to the second component. The first demodulated signal is lowpass filtered to generate a first output signal. At least one of the first amplitude and the second amplitude are adjusted to reduce the residual component with respect to the primary component.

In one embodiment, a pulse oximetry system includes a modulation signal generator. The modulation signal generator generates a first modulation signal including a first pulse at a repetition frequency having a first duty cycle. The modulation signal generator generates a second modulation signal including a second pulse which also repeats at the repetition frequency and having a second duty cycle. The second pulse can be non-overlapping with respect to the first pulse, or the second pulse can partially or completely overlap the first pulse. The first and second pulses include a plurality of components wherein a first component has a frequency corresponding to the repetition frequency and a second component has a second frequency corresponding to twice the first frequency. A first transmitter emits electromagnetic energy at a first wavelength in response to the first pulse. A second transmitter emits electromagnetic energy at a second wavelength in response to the second pulse. A detector receives electromagnetic energy at the first and second wavelengths after passing through a portion of a subject. The detector generates a detector output signal responsive to the received electromagnetic energy. The detector output signal includes a signal component responsive to attenuation of the electromagnetic energy at the first wavelength and a signal component responsive to attenuation of the electromagnetic energy at the second wavelength. A first demodulator multiplies the detector signal by a first demodulation signal and generates a first demodulated output signal. A second demodulator multiplies the detector signal by a second demodulation signal and generates a second demodulated output signal. A configuration module configures the first demodulation signal and the second demodulation signal to substantially separate the first demodulator output and the second demodulator output.

In one embodiment, the configuration module selects a phase relationship between the first demodulation signal and the second demodulation signal.

In one embodiment, the configuration module configures the first demodulation signal and the second demodulation signal using, at least in part, data obtained during a calibration period. In one embodiment, the calibration data includes first and second calibration data corresponding to the first and second demodulated output signals during a first time period, and third and fourth calibration data corresponding to the first and second demodulated output signals during a second time period. In one embodiment, the second transmitter is turned off during the first time period, and the first transmitter is turned off during the second time period.

In one embodiment, the configuration module configures the first demodulation signal and the second demodulation signal by adjusting initial parameters that define the first demodulation signal and the second demodulation signal. The configuration module adjusts the initial parameters using, at least in part, the calibration data obtained during a calibration period.

One embodiment includes an apparatus for measuring one or more blood constituents in a subject, wherein a first signal source applies a first input signal during a first time interval, a second signal source applies a second input signal during a second time interval, and a third signal source applies a second input signal during a third time interval. A detector detects a first parametric signal responsive to the first input signal passing through a portion of the subject having blood therein, a second parametric signal responsive to the second input signal passing through the portion of the subject, and a third parametric signal responsive to the third input signal passing through a portion of the subject having blood therein. The detector generates a detector output signal responsive to the first, second, and third parametric signals. A signal processor receives the detector output signal, the signal processor configured to demodulate the detector output signal by applying a first demodulation signal to a signal responsive to the detector output signal to generate a first demodulator output signal, applying a second demodulation signal to the signal responsive to the detector output signal to generate a second demodulator output signal, and applying a third demodulation signal to the signal responsive to the detector output signal to generate a third demodulator output signal. The signal processor selects the first demodulation signal, the second demodulation signal and the third demodulation signal to reduce crosstalk between the first, second, and third demodulator signals using, at least in part, first and second calibration data. The first calibration data includes calibration data wherein the first signal source, the second signal source, and the third signal source are operated singly, and wherein the second calibration data comprises calibration data wherein the first signal source, the second signal source, and the third signal source are operated in pairs.

One embodiment includes an apparatus for measuring one or more parameters in a subject. The apparatus includes, three or more sources, at least one detector configured to sense electromagnetic radiation produced by the three or more sources, an output of the at least one detector comprising a detector signal, and a signal processor. The signal processor receives the detector output signal, the signal processor configured to demodulate the detector output signal by applying a first demodulation signal to a signal responsive to the detector output signal to generate a first demodulator output signal, applying a second demodulation signal to the signal responsive to the detector output signal to generate a second demodulator output signal, and applying a third demodulation signal to the signal responsive to the detector output signal to generate a third demodulator output signal. The signal processor selects the first demodulation signal, the second demodulation signal and the third demodulation signal to reduce crosstalk between the first, second, and third demodulator signals using, at least in part, calibration data, wherein the calibration data is obtained, at least in part, by activating the three or more sources according to a set of activation patterns, wherein the number of activation patterns is greater than the number of sources in the three or more sources. In one embodiment, the activation patterns include a first set of patterns wherein each of the three or more sources is activated singly, and a second set of patterns wherein each of the three or more sources is deactivated singly. In one embodiment, the activation patterns include patterns wherein each of the three or more sources is activated one at a time. In one embodiment, the activation patterns include patterns wherein each of the three or more sources is de-activated one at a time. In one embodiment the activation patterns include patterns where more than half of the sources are activated and the remaining sources are not activated. In one embodiment the activation patterns include patterns where, at any time, more than half of the sources are not activated and the remaining sources are activated.

One embodiment includes an apparatus for measuring one or more blood constituents in a subject, where the apparatus includes a first signal source which applies a first input signal during a first time interval, a second signal source which applies a second input signal during a second time interval, a third signal source which applies a third input signal during a third time interval, a detector, and a signal processor, The detector detects a first parametric signal responsive to the first input signal passing through a portion of the subject having blood therein and detects a second parametric signal responsive to the second input signal passing through the portion of the subject, and a third parametric signal responsive to the third input signal. The detector generates a detector output signal responsive to the first, second, and third parametric signals. The signal processor which receives the detector output signal, the signal processor demodulating the detector output signal by applying a first demodulation signal to a signal responsive to the detector output signal to generate a first demodulator output signal and applying a second demodulation signal to the signal responsive to the detector output signal to generate a second demodulator output signal, the first demodulation signal determined at least in part from a first dataset wherein each of the first, second, and third sources are activated one at a time and a second dataset wherein each of the first, second, and third sources are deactivated one at a time. In one embodiment, the first dataset includes turning on only one of the first, second, or third signal sources and measuring the crosstalk between one of the parametric signals and the non-corresponding output signals. In one embodiment, at least a portion of the first dataset includes turning off only one of the first, second, or third signal sources and measuring the crosstalk between one of the parametric signals and the non-corresponding output signals.

BRIEF DESCRIPTION OF THE DRAWINGS

The present invention will be described below in connection with the accompanying figures.

DETAILED DESCRIPTION

Figure 1:
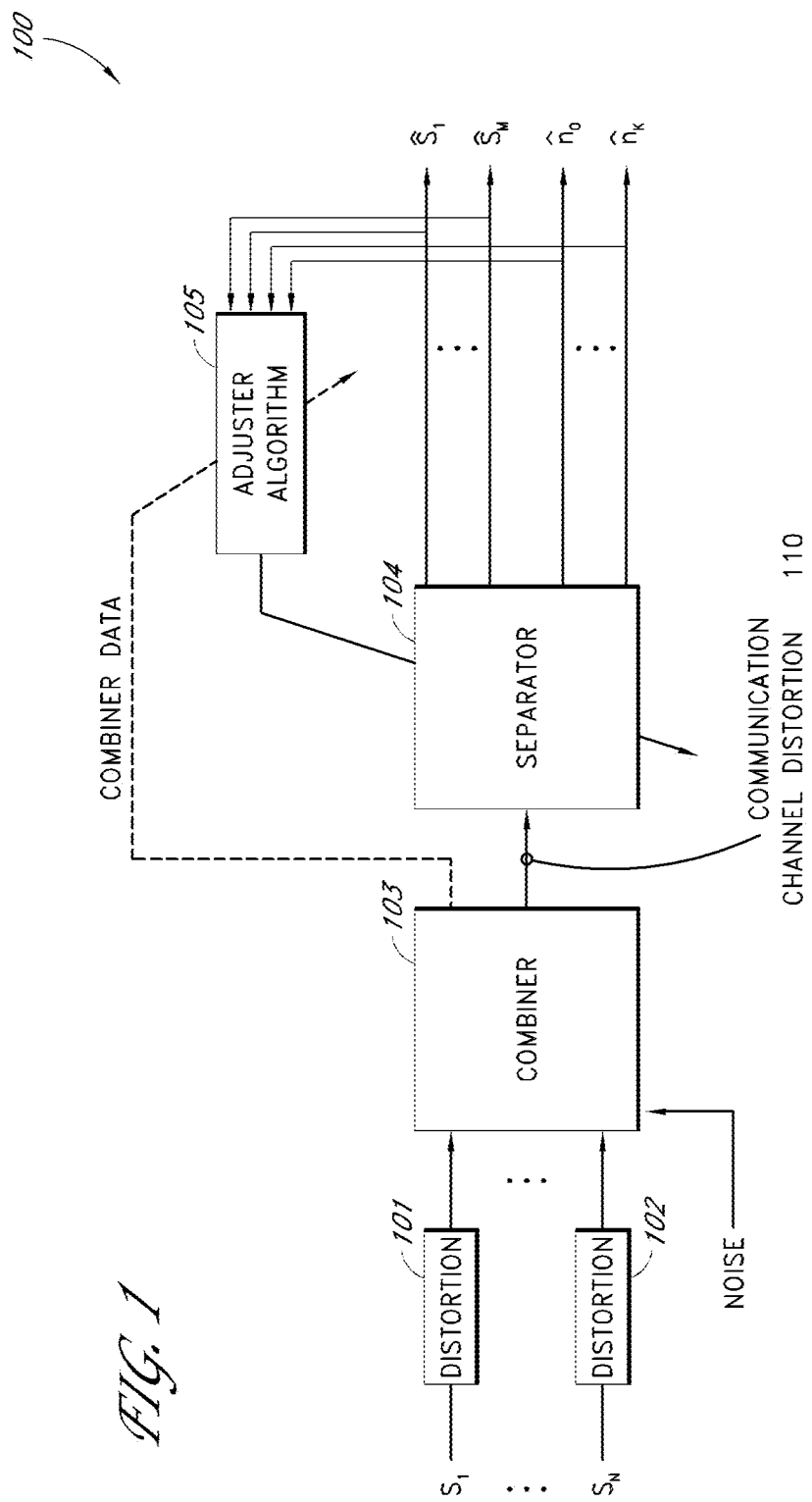
FIG. 1 is a block diagram of a multi-channel processing system that uses feedback from one or more outputs to configure the operation of a signal separator that separates a composite signal into a plurality of output signals.

FIG. 1 shows a topology of a multi-channel measurement or communication system 100. The system 100 has a signal combiner 103 for combining one or more input signals $S_1 \ldots S_N$ into a composite signal and a signal separator 104 for separating the composite signal into one or more output signals $\hat{S}_1 \ldots \hat{S}_M$. The output signals $\hat{S}_1 \ldots \hat{S}_M$ can include estimates of the input signals $S_1 \ldots S_N$. The input signals $S_1 \ldots S_N$ are corrupted by pre-combination distortion 101-102 respectively, and optionally, by combination distortion in the signal combiner 103. The combiner 103 combines the N input signals into a composite signal (or composite signals). The combiner 103 can combine signals by addition, subtraction, multiplication, division, modulation, non-linear processes, linear processes, estimation, combinations thereof, etc. The composite signal is provided through a communication channel to the separator 104. The composite signal is distorted by communication channel distortion 110. The separator 104 separates the composite signal into M output signals, where M can be less than N, greater than N, or equal to N. In one embodiment, the separator also provides one or more additional output signals $\hat{n}_0 \ldots \hat{n}_K$ corresponding to estimates of other signals, such as, for example, noise signals, error signals, etc.

Due to errors in the system 100, the output signals $\hat{S}_1 \ldots \hat{S}_M$ are typically not exact copies of the input signals, but rather are estimates of the input signals. The accuracy of these estimates is a measure of system performance. The pre-combination distortion 101-102, the combiner distortion, and/or the channel distortion 110 tend to introduce crosstalk between the channels and thereby corrupt the output signals. The pre-combination distortion 101-102, combiner distortion, and the channel distortion 110 can be caused by variations in manufacturing tolerances, delay, movement, temperature effects, degradation of components due to age or other factors, noise, etc.

A module 105 is provided to configure the separator 104 to improve the quality of the separation function and thereby improve the quality of the output signals. One or more of the output signals from the separator are provided to the module 105 to provide feedback regarding the quality of the output signals and/or feedback regarding the operation of the separator 104. The module 105 uses feedback from one or more of the output signals $\hat{S}_1 \ldots \hat{S}_M$ (and, optionally, the output signals $\hat{n}_0 \ldots \hat{n}_K$) to monitor the quality of the separation function and to provide control information to control the operation of the separator. In one embodiment, the module 105 is configured by using configuration data obtained from the combiner 103. Such configuration data can be obtained by calibration procedures that test the operation of the combiner 103 before or during system use.

In one embodiment, the module 105 configures demodulators in the signal separator 104 using, at least in part, calibration data obtained during a calibration period. For example, in one embodiment involving a two channel system, the calibration data includes first and second calibration data corresponding to the first and second output signals during a first time period, and third and fourth calibration data corresponding to the first and second demodulated output signals during a second time period. In one embodiment, the second transmitter is turned off during the first time period, and the first transmitter is turned off during the second time period. In one embodiment, the module 105 configures the first demodulation signal and the second demodulation signal by adjusting initial parameters that define the first demodulation signal and the second demodulation signal. The configuration module adjusts the initial parameters using, at least in part, the calibration data obtained during a calibration period.

Figure 2:
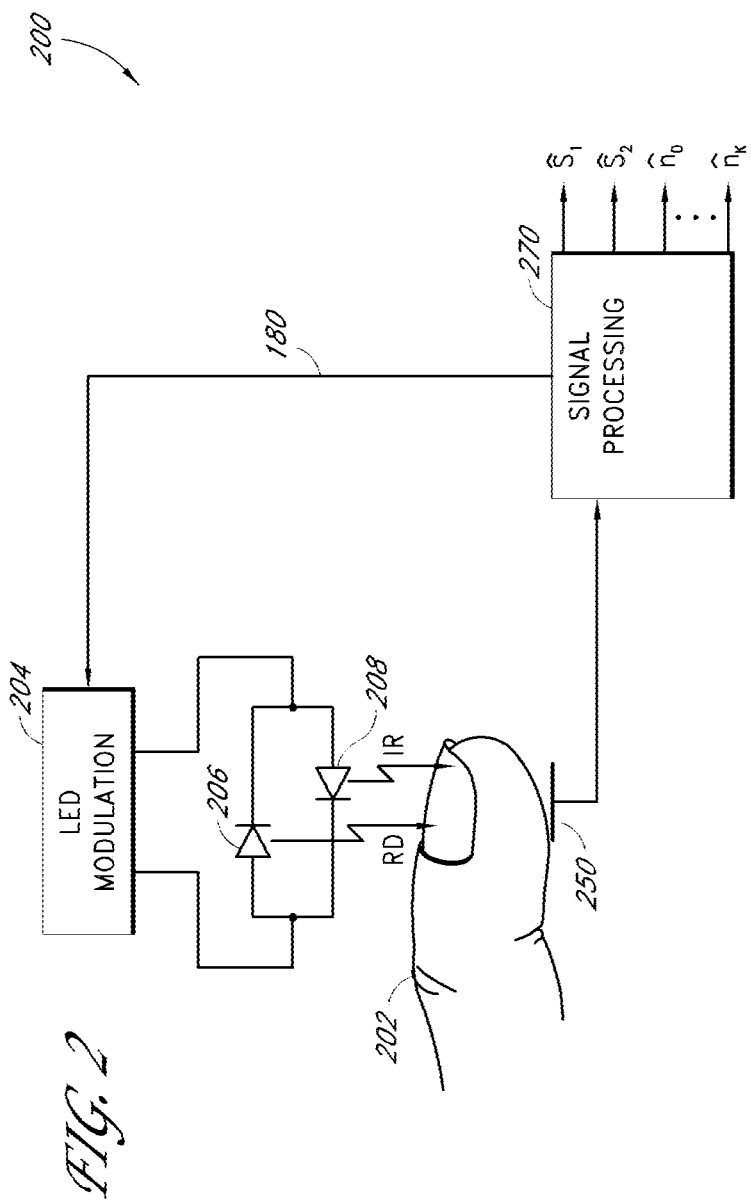
FIG. 2 is a block diagram of a two-channel signal processing system to determine blood oxygen saturation in a subject, wherein illumination is provided by back-to-back Light-Emitting Diodes (LEDs).

FIG. 2 is a block diagram of a two-channel signal processing system 200 that fits the general topology shown in FIG. 1. The system 200 is configured to determine one or more blood constituents in a subject, such as, for example, a human subject. In the example presented, the measurements are performed on a portion of the subject, such as a finger 202. An LED modulation circuit 204 drives a pair of back-to-back light emitting diodes (LEDs) 206, 208 by applying a periodic signal to the two light emitting diodes 206, 208. Light from the diodes 206, 208 passes through the finger 202 and is detected by a detector 250. An output from the detector 250 is provided to a signal processing block 270. A control output from the signal processing block 270 is provided to the LED modulation circuit 204. The signal processing block 270 also provides outputs $\hat{S}_1$ and $\hat{S}_2$ corresponding to the light detected from the diodes 206, 208, and, optionally, output signals $\hat{n}_0 \ldots \hat{n}_K$, corresponding to estimates of noise or other signals.

In one embodiment, the LED 206 is selected to emit electromagnetic energy in the red visible light range, and has a wavelength of, for example, approximately 660 nanometers. The LED 208 is selected to emit electromagnetic energy in the infrared range, and has a wavelength of, for example, approximately 905 nanometers. The LED modulation circuit 204 supplies current to activate the LEDs 206 and 208. Each LED is activated for a time period T which can be different for the different LEDs. The pulses from the LEDs 206 and 208 repeat with a periodicity T.

Figure 3:
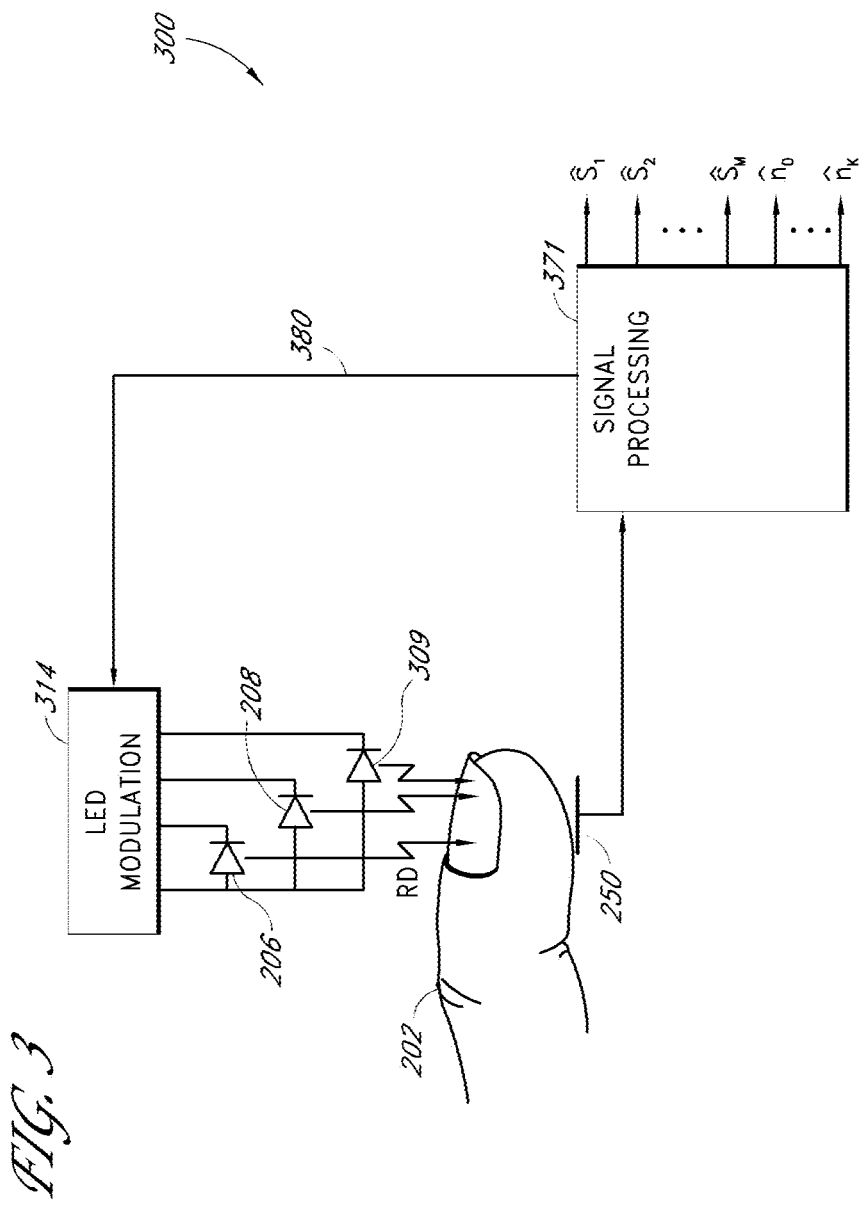
FIG. 3 is a block diagram of a multi-channel signal processing system to determine blood constituents (e.g., oxygen saturation) in a subject, wherein illumination is provided by N diodes or illumination sources.

FIG. 3 is a block diagram of a multi-channel signal processing system 300 that also fits the topology shown in FIG. 1. Like the system 200, the system 300 is configured to determine blood oxygen saturation or other blood constituents in a subject, such as, for example, a human subject. In FIG. 3, an LED modulation circuit 314 drives N diodes, where N is two or greater, thus allowing greater flexibility than the system 200. In FIG. 3, the diodes 206 and 208 are shown, along with an N'th diode 309, it being understood that the diode 309 is omitted if N=2. The LED modulation circuit 314 is configured to allow the diodes 206, 208, and 309 to be driven independently such that the diodes can be driven at separate times or in overlapping time periods if desired. Light from the diodes 206, 208, 309 passes through the finger 202 and is detected by the detector 250. The output from the detector 250 is provided to a signal processing block 371. A control output from the signal processing block 371 is provided to the LED modulation circuit 314. The signal processing block 371 also provides outputs $S_1$ through SM, where M is greater than or equal to one, but need not be equal to N.

Figure 4:
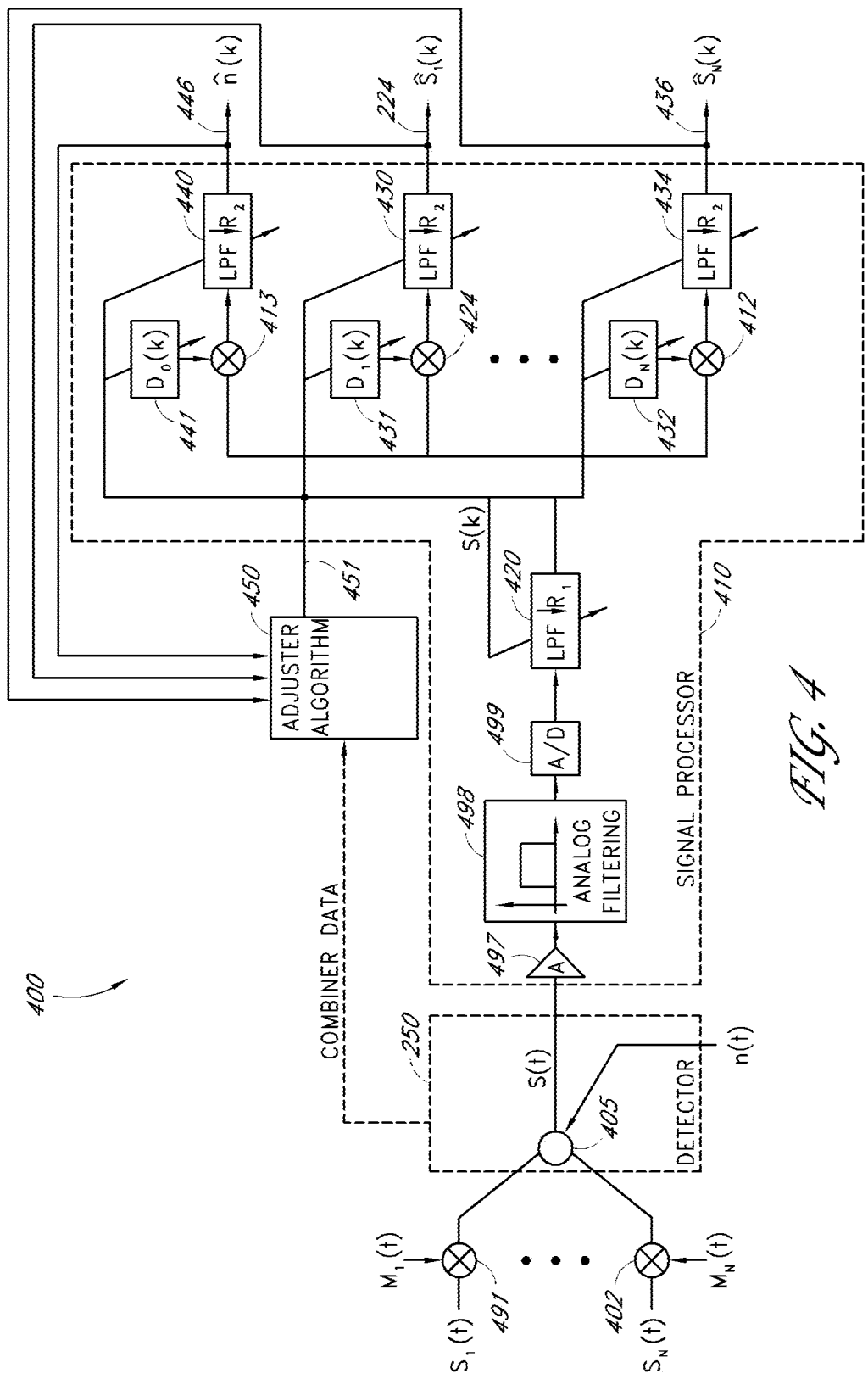
FIG. 4 is a block diagram of a specific embodiment of the multi-channel processing system of FIG. 1.

FIG. 4 shows one embodiment of an adjustable multi-channel modulator/demodulator system 400. The system 400 is based on the topology of the system 100 and can be used in a system for measuring blood constituents (e.g., pulse oximetry, carboxyhemoglobin, etc.) as shown in FIGS. 2 and 3. In the system 400, an input $S_1(t)$ and a modulation input $M_1(t)$ are provided to a first modulator 491. A signal input $S_N(t)$ and a modulation input $M_N(t)$ are provided to an $N^{th}$ modulator 402.

The photodetector 250 is modeled as an adder 405. The outputs of the modulators 491 and 402 are added together in the adder 405, in the presence of noise n(t) to generate a composite signal M(t) where:

$$S(t)=S_1(t)M_1(t)+ \ldots +S_N(t)M_N(t)+n(t) \quad (1)$$

The S(t) signal output of the adder 405 (i.e., the output of the detector 250) is applied to the input of a signal-processing block 410. Within the signal-processing block 410, the signal S(t) is passed through an amplifier 497 and through an analog bandpass filter 498. The analog bandpass filter 498 provides anti-aliasing and removal of low frequency noise and DC. The desired signal components in the signals $S_i(t)$ are frequency shifted by the operation of the modulation signals $M_i(t)$ and are passed by the analog bandpass filter 498.

The output of the analog bandpass filter 498 is sampled by an analog-to-digital converter 499 and converted therein to digital signals and provided to an input of an optional decimation block 420.

The filtered (and, optionally, decimated) signal S(t) is sampled to produce a sampled-data signal S(k) that is provided to the first input of the first mixer 424, to the first input of the N'th mixer 412, and to the first input of a noise channel mixer 413. A first demodulating signal $D_1(k)$ is provided to a second input of a first mixer 424 from a signal generator 431. The $N^{th}$ demodulating signal $D_N(k)$ is provided to an $N^{th}$ mixer 412 from an output of a signal generator 432. The noise demodulating signal $D_0(k)$ is provided to the noise channel mixer 413 from an output of a signal generator 441. A control input to each of the signal generators 431, 432, and 441 is provided by the output of the adjuster algorithm 450. In yet another embodiment, the adjuster algorithm 450 may also be controlled by other signal processing elements downstream of the signal processor 400.

The outputs of the mixers 413, 424, and 412 are provided as respective inputs to decimation blocks 440, 430, and 434 respectively. Each of the decimation blocks 440, 430, and 434 has a control input provided by the output of the adjuster algorithm block 450. The output of the decimation block 440 is an estimate of the signal n(t) and it is provided to an input of the adjuster algorithm block 450. In an alternate embodiment, the signal estimates $\hat{S}_i(k)$ are also provided to the adjuster algorithm block 450.

An output of the decimator 430 is a signal $\hat{S}_1(k)$, which, as discussed above, is an estimate of the signal $S_1(k)$ (where $S_1(k)$ corresponds to a sampled-data representation of $S_1(t)$). Likewise, the output of the decimation block 434 is an estimate of the signal $S_N(t)$. As shown above, the selection of the demodulating signals $D_i(t)$ for i=0 . . . N in accordance with the present invention substantially reduces or eliminates the effects of noise in the output signals $\hat{S}_i(k)$ and n(k), and also substantially reduces or eliminates crosstalk between the signals.

When the system 400 is used in connection with a blood constituent measurement system as shown in FIGS. 2 and 3, the red LED 206 provides a light intensity represented as $I_{RD}$, and the infrared LED 208 provides a light intensity represented as $I_{IR}$. The effects of turning the LEDs 206, 208 on and off on a periodic bases are modeled by the first multiplier or modulator 290 which applies a first modulation signal $M_1(t)$ to the red light intensity to generate a modulated red signal $I_{RDMOD}(t)$ and by a second multiplier the modulator 292 which applies a second modulation signal $M_2(t)$ to the infrared light intensity to generate a modulated infrared signal $I_{IRMOD}(t)$. The modulated light red signal and the modulated infrared signal are applied to the finger 202, or other body portion, as described above. The blood in the finger 202 has a volume and scattering components, which vary throughout each cardiac cycle. The blood carries oxygen and other materials therein. The oxygen content is a function of both the blood volume and the concentration of the oxygen in the blood volume. The concentration of the oxygen in the blood volume is generally measured as blood oxygen saturation for reasons which are described in full in U.S. Pat. Nos. 5,482,036 and 5,490,505, both of which are hereby incorporated by reference in their entirety. As further described in the two referenced patents, the blood oxygen saturation is determined by comparing the relative absorption of the red light and the infrared light in the finger 202. The comparison is complicated by the noise caused by movement, ambient light, light scattering, and other factors. The signals $S_1(t)$ and $S_2(t)$ represent the effect of the time-varying volume and scattering components of the blood in the finger 202 on the red light and the infrared light, respectively, passing through the finger 202 from the LEDs 206, 208 to the detector 250.

As shown in FIG. 4, a set of N+1 signals $S_i[k]$ i=1 . . . N, and n(k) are sampled at a desired sample rate. The signals are combined according to the formula:

$$S(k)=M_1(k)S_1(k)+ \ldots +M_N(k)S_N(k)+n(k) \quad (2)$$

In one embodiment, each of the decimators 420, 440, 430, and 434 includes a digital lowpass filter and a sample rate compressor. In one embodiment, the characteristics of the digital lowpass filters (e.g., the number of filter coefficients and values of the filter coefficients) and the sample rate compression factor of each decimator are fixed. In one embodiment, the characteristics of the digital lowpass filters (e.g., the number of filter coefficients or values of the filter coefficients) and the sample rate compression factor of each decimator are provided by the adjustment algorithm 450. The signal generators 431, 432 and 441 generate the demodulation sequences for the demodulators 424, 412, and 413 respectively. The demodulation sequences produced by the signal generators 431, 432 and 441 are controlled by the adjuster algorithm 450.

In one embodiment, the adjuster algorithm 450 adjusts the pre-demodulation decimation rate $R_1$ (in the demodulator 420), and the post-demodulation decimation rate $R_2$ (in the demodulators 430, 434 and 440) according to the noise in the noise estimate $\hat{n}(k)$ and (optionally) according to the signals $\hat{S}_i(k)$. The product $R_1R_2$ is the total decimation rate from the signal $S(k)$ at the output of the A/D converter 499 to the signals $\hat{S}_i(k)$ at the output of the signal processing block 400. The adjuster algorithm may adjust $R_1$ and $R_2$ such that the product $R_1R_2$ varies, or the adjuster algorithm may adjust $R_1$ and $R_2$ such that the product $R_1R_2$ is substantially constant. Typically, the adjuster algorithm will keep the $R_1R_2$ product constant so that the signal processing blocks downstream of the signal processor 400 will operate at a substantially constant sample rate.

In one embodiment, the adjuster algorithm 450 adjusts the demodulation signals $D_i(k)$ to reduce or eliminate crosstalk. In one embodiment, the adjuster algorithm 450 reduces crosstalk by configuring the demodulators, as discussed in more detail below.

One skilled in the art will recognize that the lowpass filters provided in connection with the decimation blocks can provide other filter functions in addition to lowpass filtering. Thus, for example, the lowpass filters 420, 430, 440, and 450, and the decimators 420, 430, 434, and 440 can provide other filter functions (in addition to lowpass filtering) such as, for example, bandpass filtering, bandstop filtering, etc. Moreover, the post-demodulation decimation rate $R_2$ need not be the same for each output channel. Thus, for example, in FIG. 4, the decimator 440 can have a first decimation rate $R_2=r_1$ while the decimators 430 and 434 have a second decimation rate $R_2=r_2$.

The demodulators above are described in terms of digital signal processing on sampled data. Thus, the demodulator signals are written $D_i(k)$. The demodulators and the filtering associated with the demodulators can be done in using analog processing (using time-domain demodulator signals $D_i(t)$) or on sampled data signals (using digital-domain demodulator signals $D_i(k)$). For convenience, the following development describes the demodulator signals primarily in the time domain, with the understanding that the modulators can be implemented using digital signal processing or analog processing.

The characteristics of the demodulation signals $D_1(t)$ and $D_2(t)$ affect how much crosstalk is seen in the output signals. In an diagonal system, that is, when the demodulator has been diagonalized, there is, ideally, no crosstalk. The first output signal $\hat{S}_1(t)$ is an estimate (or approximation) to the signal $S_1(t)$. Similarly, the second output signal $\hat{S}_2(t)$ is an estimate (or approximation) to the signal $S_2(t)$. When the composite signal $S(t)$ is a linear combination of the signals $S_i(t)$, then the relationship between the signals $S_i(t)$ and the signals $\hat{S}_i(t)$. When $M_1=\cos \omega t$, $M_2=\sin \omega t$, $n(t)=0$, and there is no distortion (e.g., no pre-combination, combiner, or channel distortion) then:

$$S(t)=S_1(t)\cos \omega t+S_2(t)\sin \omega t \qquad (3)$$

Then:

$$\hat{S}_1(t)=LP[D_1(t)S(t)] \qquad (4)$$

$$\hat{S}_2(t)=LP[D_2(t)S(t)] \qquad (5)$$

If:

$$D_1(t) = 2\cos\omega t \qquad (6)$$

$$D_2(t) = 2\sin\omega t \qquad (7)$$

then
$$\begin{aligned} D_1(t)S(t) &= 2S_1(t)\cos^2\omega t + 2S_2(t)\sin\omega t\cos\omega t \\ &= S_1(t) - S_1(t)\cos 2\omega t + S_2(t)\sin 2\omega t \end{aligned} \qquad (8)$$

After lowpass filtering to remove the terms with a frequency of 2 ωt and higher $$\hat{S}_1(t)=S_1(t) \qquad (9)$$

Similarly for $$\hat{S}_2(t) = LP[D_2(t)S(t)] \qquad (10)$$

then
$$\begin{aligned} D_2(t)S(t) &= 2S_1(t)\sin\omega t\cos\omega t + 2S_2(t)\sin^2\omega t \\ &= S_2(t) - S_2(t)\cos 2\omega t + S_1(t)\sin 2\omega t \end{aligned} \qquad (11)$$

After lowpass filtering to remove the terms with a frequency of 2 ωt $$\hat{S}_2(t)=S_2(t) \qquad (12)$$

In the above analysis, it was assumed that there are no time delays or phase shifts in the signal $S(t)$, and thus, configuration is relatively straightforward.

When an unknown delay (or phase error) is introduced, then the signals are no longer diagonal. Consider, for example, the situation when a delay $\Delta$ is introduced into the composite signal. Then:

$$S(t)=\cos \omega(t-\Delta)S_1(t-\Delta)+\sin \omega(t-\Delta)S_2(t-\Delta)$$

It then follows that:

$$\begin{aligned} \hat{S}_1(t) &= LP[2\cos\omega t(\cos\omega(t-\Delta)S_1(t-\Delta) + \sin\omega(t-\Delta)S_2(t-\Delta))] \\ &= LP[2\cos\omega t(\cos\omega t\cos\omega\Delta + \sin\omega t\sin\omega\Delta)S_1(t-\Delta)] + \\ &\quad LP[2\cos\omega t(\sin\omega t\cos\omega\Delta - \cos\omega t\sin\omega\Delta)S_2(t-\Delta)] \\ &= \cos\omega\Delta S_1(t-\Delta) - \sin\omega\Delta S_2(t-\Delta) \end{aligned}$$

The above equations can be expressed in matrix form as:

$$\begin{bmatrix} \hat{S}_1(t) \\ \hat{S}_2(t) \end{bmatrix} = \begin{bmatrix} \cos\omega\Delta & -\sin\omega\Delta \\ \sin\omega\Delta & \cos\omega\Delta \end{bmatrix} \begin{bmatrix} S_1(t-\Delta) \\ S_2(t-\Delta) \end{bmatrix} \qquad (13)$$

$$\text{Then } \begin{bmatrix} S_1(t-\Delta) \\ S_2(t-\Delta) \end{bmatrix} = \begin{bmatrix} \cos\omega\Delta & \sin\omega\Delta \\ -\sin\omega\Delta & \cos\omega\Delta \end{bmatrix} \begin{bmatrix} \hat{S}_1(t) \\ \hat{S}_2(t) \end{bmatrix} \qquad (14)$$

The above equation can be expressed as $$\begin{aligned} \begin{bmatrix} S_1(t-\Delta) \\ S_2(t-\Delta) \end{bmatrix} &= \begin{bmatrix} \cos\omega\Delta & -\sin\omega\Delta \\ \sin\omega\Delta & \cos\omega\Delta \end{bmatrix} LP\begin{bmatrix} D_1(t)S(t) \\ D_2(t)S(t) \end{bmatrix} \\ &= \left[\begin{bmatrix} \cos\omega\Delta & \sin\omega\Delta \\ -\sin\omega\Delta & \cos\omega\Delta \end{bmatrix} \begin{bmatrix} D_1(t) \\ D_2(t) \end{bmatrix}\right] S(t) \\ &= \left[\begin{bmatrix} \bar{D}_1(t) \\ \bar{D}_2(t) \end{bmatrix}\right] S(t) \end{aligned} \qquad (15)$$

where $\begin{aligned}\bar{D}_1(t) &= \cos\omega\Delta D_1(t) + \sin\omega\Delta D_2(t) \\ &= 2\cos\omega\Delta\cos\omega t + 2\sin\omega\Delta\sin\omega t\end{aligned}$ and similarly for $\overline{D}_2(t)$. Thus the modified demodulation functions $\overline{D}_1(t)$ and $\overline{D}_2(t)$ can be expressed as a linear combination of basis functions. If the time delay $\Delta$ can be predicted, then the demodulator functions can be calculated and programmed into the communication system. However, in many cases the time delay $\Delta$ is not known or changes over time. As described below, the demodulator functions can be determined by system calibration procedures.

When an unknown phase shift (or phase error) is introduced, then there may be crosstalk in the system. Consider, for example, the situation when a phase error $\phi_1$ occurs in the signal $S_1(t)$ and a phase error $\phi_2$ occurs in the signal $S_2(t)$. The phase errors can be caused by intrinsic properties of the components, intrinsic properties of the system, component variations, time delays, etc. In the presence of the phase errors:

$$D_1(t)S(t) = 2A_1S_1(t)\sin(\omega t + \phi_1)\sin\omega t + 2A_2S_2(t)\cos(\omega t + \phi_2)\sin\omega t \quad (16)$$

$$= 2A_1S_1(t)\sin\omega t[\sin\omega t\cos\phi_1 + \cos\omega t\sin\phi_1] +$$

$$2A_2S_2(t)\sin\omega t[\cos\omega t\cos\phi_2 + \sin\omega t\sin\phi_2]$$

$$= A_1S_1(t)\cos\phi_1 - A_1S_1(t)\cos\phi_1\cos 2\omega t +$$

$$A_1S_1(t)\sin\phi_1\sin 2\omega t + A_2S_2(t)\cos\phi_2\sin 2\omega t -$$

$$A_2S_2(t)\sin\phi_2 + A_2S_2(t)\sin\phi_2\cos 2\omega t$$

Thus, after lowpass filtering $$\hat{S}_1(t) = A_1S_1(t)\cos\phi_1 - A_2S_2(t)\sin\phi_2 \quad (17)$$

The above equation shows crosstalk because $\hat{S}_1(t)$ depends in part on components of $S_2(t)$ when $A_2 \neq 0$ and $\phi_2 \neq n\pi$ where $n=0, \pm 1, \pm 2 \ldots$.

Similarly, $$\hat{S}_2(t) = A_1S_1(t)\sin\phi_1 + A_2S_2(t)\cos\phi_2 \quad (18)$$

The above equations can be expressed in matrix form as:

$$\begin{bmatrix} \hat{S}_1(t) \\ \hat{S}_2(t) \end{bmatrix} = \begin{bmatrix} A_1\cos\phi_1 & -A_2\sin\phi_2 \\ A_1\sin\phi_1 & A_2\cos\phi_2 \end{bmatrix} \begin{bmatrix} S_1(t) \\ S_2(t) \end{bmatrix} \quad (19)$$

After inversion $$\begin{bmatrix} S_1(t) \\ S_2(t) \end{bmatrix} = \frac{1}{\cos(\phi_1-\phi_2)} \begin{bmatrix} \frac{\cos\phi_2}{A_1} & \frac{\sin\phi_1}{A_1} \\ -\frac{\sin\phi_2}{A_2} & \frac{\cos\phi_1}{A_2} \end{bmatrix} \begin{bmatrix} \hat{S}_1(t) \\ \hat{S}_2(t) \end{bmatrix} \quad (20)$$

$$\begin{bmatrix} S_1(t) \\ S_2(t) \end{bmatrix} = \frac{1}{\cos(\phi_1-\phi_2)} \begin{bmatrix} \frac{\cos\phi_2}{A_1} & \frac{\sin\phi_1}{A_1} \\ -\frac{\sin\phi_2}{A_2} & \frac{\cos\phi_1}{A_2} \end{bmatrix} \begin{bmatrix} D_1(t) \\ D_2(t) \end{bmatrix} S(t) \quad (21)$$

Then $\begin{bmatrix} S_1(t) \\ S_2(t) \end{bmatrix} = \begin{bmatrix} \overline{D}_1(t) \\ \overline{D}_2(t) \end{bmatrix} S(t) \quad (22)$ Where $\overline{D}_i(t)$ are modified demodulation functions, given by:

$$\begin{bmatrix} \overline{D}_1(t) \\ \overline{D}_2(t) \end{bmatrix} = \frac{1}{\cos(\phi_1-\phi_2)} \begin{bmatrix} \frac{\cos\phi_2\sin\omega t + \sin\phi_1\cos\omega t}{A_1} \\ \frac{-\sin\phi_2\sin\omega t + \cos\phi_1\cos\omega t}{A_2} \end{bmatrix} \quad (23)$$

The modified demodulation functions have the form $$\overline{D}_i(t) = \sum_{j=1}^{N} \alpha_j \Phi_j(t) \quad (24)$$

Choosing the coefficients $\alpha_j$ to eliminate crosstalk configures the modulator.

In one embodiment, the coefficients $\alpha_j$ can be fixed coefficients computed using known properties of the system. However, as system properties change over time, such fixed coefficients may lead to unacceptably high levels of crosstalk. Moreover, variations from device to device may cause the fixed coefficients to give unacceptably high levels of crosstalk.

Higher performance (that is, lower crosstalk) can be obtained by computing the coefficients as part of a system calibration or initialization procedure. Such calibration can be performed during system startup (e.g., when the system is turned on, or when the system begins processing data, etc.) and/or at regular intervals. In one embodiment, the adjuster algorithm 450 computes the coefficients $\alpha_j$ from the calibration data. In one embodiment, the coefficients $\alpha_j$ are chosen by making four calibration-type measurements to measure four parameters $\xi_{11}$, $\xi_{12}$, $\xi_{21}$, and $\xi_{22}$, where:

$$\xi_{11} = \hat{S}_1|_{S_1=A, S_2=0} = Aa_1\cos\phi_1 \quad (25)$$

$$\xi_{12} = \hat{S}_1|_{S_1=0, S_2=B} = -Ba_2\sin\phi_2 \quad (26)$$

$$\xi_{21} = \hat{S}_2|_{S_1=A, S_2=0} = Aa_1\sin\phi_1 \quad (27)$$

$$\xi_{22} = \hat{S}_2|_{S_1=0, S_2=B} = Ba_2\cos\phi_2 \quad (28)$$

where A and B are amplitudes. Then $$a_1 = \frac{\sqrt{\xi_{11}^2 + \xi_{21}^2}}{A} \quad (29)$$

$$a_2 = \frac{\sqrt{\xi_{12}^2 + \xi_{22}^2}}{B} \quad (30)$$

$$\tan\phi_1 = \frac{\xi_{21}}{\xi_{11}} \quad (31)$$

$$\tan\phi_2 = -\frac{\xi_{12}}{\xi_{22}} \quad (32)$$

From the above equations, it is evident that crosstalk depends only on $\phi_1$ and $\phi_2$. Moreover, $\phi_1$ and $\phi_2$ can be chosen to eliminate crosstalk without knowing A or B. This is useful for systems such as pulse oximetry systems where absolute measurements of a channel are difficult or impractical, but where relative measurements (e.g., channel-to-channel measurements) are practical.

The demodulation signals $D_i(t)$ can be generated using the values of $\phi_1$ and $\phi_2$ from the above equations. Alternatively, the demodulation signals $D_i(t)$ can be generated from quadrature components as:

$$D_1(t) = b_{11}\sin\omega t + b_{12}\cos\omega t \quad (33)$$

$$D_2(t) = b_{21}\sin\omega t + b_{22}\cos\omega t \quad (34)$$

where the coefficients $b_{ij}$ are computed from $\phi_1$ and $\phi_2$.

In one embodiment, the demodulation functions are adapted from baseline coefficients, which are then improved through a calibration or initialization procedure to produce actual coefficients. The baseline coefficients are typically obtained from known properties of the system. The actual coefficients are usually relatively close in value to the baseline coefficients. This provides one way to assess the operational status of the system and to evaluate the calibration procedure. In one embodiment, if the actual coefficients are too different from the baseline parameters then it is assumed that the calibration procedure failed in some manner or that the equipment has failed in some manner, and appropriate measures can be taken (e.g., alert the operator, sound a warning, etc.)

To find the actual coefficients, the demodulation functions are initially given by:

$$D_1(t) = \alpha_{11} \sin \omega t + \alpha_{12} \cos \omega t \quad (35)$$

$$D_2(t) = \alpha_{21} \sin \omega t + \alpha_{22} \cos \omega t \quad (36)$$

Where the coefficients $\alpha_{ij}$ are the baseline coefficients determined from known or assumed properties of the signal S(t). For example, in one embodiment $\alpha_{ij} = \delta_{ij}$. In one embodiment, where initial estimates are available for $\phi_1$ and $\phi_2$, then the values of $\alpha_{ij}$ can be computed as discussed above.

The crosstalk reduction obtained using demodulation functions based on the coefficients $\alpha_{ij}$ can often be improved by computing new coefficients $\overline{\alpha}_{ij}$ and corresponding new demodulation functions $\overline{D}_i(t)$ where:

$$\overline{D}_1(t) = \alpha_{11} \sin \omega t + \overline{\alpha}_{12} \cos \omega t \quad (37)$$

$$\overline{D}_2(t) = \alpha_{21} \sin \omega t + \overline{\alpha}_{22} \cos \omega t \quad (38)$$

The process of finding the coefficients $\overline{\alpha}_{ij}$ begins by measuring two data sets, $x_1(t)$ and $x_2(t)$, as follows:

$$x_1(t) = S(t)|_{S_1=A, S_2=0} \quad (39)$$

$$x_2(t) = S(t)|_{S_1=0, S_2=B} \quad (40)$$

The data sets $x_1(t)$ and $x_2(t)$ are used to enforce the following constraint:

$$\int_0^{nT} x_i(t) \overline{D_i}(t) d = 0 \quad (41)$$

where i=1, 2, n=1, 2, 3 . . . , and T is a time period corresponding to one complete modulation cycle. From the above constraint and the definitions of the demodulation functions, it follows that:

$$\overline{\alpha}_{11} \int_0^{nT} x_1(t) \sin \omega t dt + \overline{\alpha}_{12} \int_0^{nT} x_1(t) \cos \omega t dt = 0 \quad (42)$$

$$\overline{\alpha}_{21} \int_0^{nT} x_2(t) \sin \omega t dt + \overline{\alpha}_{22} \int_0^{nT} x_2(t) \cos \omega t dt = 0 \quad (43)$$

It is convenient to define $$\gamma_{11} = \int_0^{nT} x_1(t) \sin \omega t dt \quad (44)$$

$$\gamma_{12} = \int_0^{nT} x_1(t) \cos \omega t dt \quad (45)$$

$$\gamma_{21} = \int_0^{nT} x_2(t) \sin \omega t dt \quad (46)$$

$$\gamma_{22} = \int_0^{nT} x_1(t) \cos \omega t dt \quad (47)$$

and to define $$\beta_0 = \frac{\gamma}{\left[\sum_k \gamma_{ik}^2\right]^{1/2}} \text{ where} \quad (48)$$

$$\sum_k \beta_{ik}^2 = 1 \quad (49)$$

Then $\overline{\alpha}_{11} \overline{\beta}_{11} + \overline{\alpha}_{12} \overline{\beta}_{12} = 0 \quad (50)$ $\overline{\alpha}_{21} \overline{\beta}_{21} + \overline{\alpha}_{22} \overline{\beta}_{22} = 0 \quad (51)$ In one embodiment, to reduce crosstalk, it is desired to find the coefficients $\overline{\alpha}_{ij}$ closest (in the sense of minimizing some specified error, such as, for example, a least squared error) to the coefficients $\overline{\alpha}_{ij}$ such that the above constraints are satisfied. One solution, obtained by minimizing the least squared error is:

$$\overline{\alpha}_{ij} = \alpha_{ij} - \left(\sum_k \alpha_{ik} \beta_{ik}\right) \beta_{ij} \quad (52)$$

The term in parentheses can be described as the baseline crosstalk.

One of ordinary skill in the art will recognize that optimization methods other than least squares can be used. The solution methods for configuration are, for simplicity, described above in terms of a two-channel system. Using the above teachings, the extension to multi-channel systems is straightforward.

In one embodiment, systems with more than two channels can be calibrated using data from multiple calibration data sets. The calibration data sets can use different combinations of sources and/or different activation patterns of sources to provide additional information for calibration. Thus for example, in one embodiment, calibration measurements are obtained by activating the sources one at a time (with the other sources off) and calibration measurements are also obtained by deactivating one source at a time (with the other sources on). Both sets of calibrations measurements can then be used (in whole or in part) to calculate demodulation information.

In one such procedure for a system with 8 sources, data sets $x_1$-$x_{16}$ are obtained using the following activation patterns as follows:

$x_1$ = LED 1 on (others off)

$x_2$ = LED 2 on (others off)

⋮

-continued $x_8 = LED\ 8$ on (others off)

$x_9 = LED\ 1$ off (others on)

$x_{10} = LED\ 2$ off (others on)

$\vdots$ $x_{16} = LED\ 8$ off (others on)

Then using the functions:

$$\phi_{2j,k} = \sin\left(2\pi f_j \frac{k}{T} + HW_j\right)$$

$$\phi_{2j+1,k} = \cos\left(2\pi f_j \frac{k}{T} + HW_j\right)$$

where $HW_j$ are hardware coefficients (such as, for example, known delays in the system), and $f_j$ are the modulation frequencies, then the $\zeta$ matrix can be computed as $$\varsigma_{i,j} = \sum_{k=1}^{\#points} x_{i,k}\phi_{j,k}$$

$$\varsigma = \underbrace{\begin{bmatrix} \varsigma_{1,1} & \cdots & \cdots & \varsigma_{1,8} \\ \vdots & & & \vdots \\ \varsigma_{8,1} & & & \varsigma_{8,8} \\ \vdots & & & \vdots \\ \varsigma_{16,1} & \cdots & \cdots & \varsigma_{16,8} \end{bmatrix}}_{2\cdot order} \Big\}\text{number of channels}$$

Then, under the assumption that the number of channels is equal to 2 time the order, to compute the demodulation coefficients for channel j' the $\Lambda$ matrix can be computed as:

$$\Lambda = \underbrace{\begin{bmatrix} \varsigma_{1,1} & \cdots & \varsigma_{1,8} \\ \vdots & & \vdots \\ \varsigma_{8,1} & \cdots & \varsigma_{8,8} \\ \varsigma_{8+j',1} & \cdots & \varsigma_{8+j',8} \end{bmatrix}}_{2\cdot order} \Big\}2\text{order}+1$$

The QR decomposition of $\Lambda$ returns Q and R matrices where:

$Q$ is (2×order+1)×(2×order+1)

$R$ is (2×order+1)×(2×order)

Define $j = 1 \ldots 8 = 2\times\text{order}$ $k = 1 \ldots 8 = 2\times\text{order}$ $A_{j,k} = R_{j,k} b_k = Q_{j',k} \leftarrow j'\text{th}$ row but only 2×order values Then calculate $\vec{\beta}$ where $$\beta_{2\cdot order} = \frac{b_{2\cdot order}}{A_{2\cdot order, 2\cdot order}}$$

and for $i=2$ order$-1, \ldots, 1$ $$\beta_i = \frac{\left(b_i - \sum_{j=i+1}^{2\cdot order} A_{i,j}\beta_j\right)}{A_{i,j}}$$

After normalizing $\vec{\beta}$ by $$\hat{\beta} = \frac{\vec{\beta}}{|\vec{\beta}|}$$

Then the new demodulation coefficient vectors are given by:

$$\hat{\alpha}_j = (\vec{\alpha}_j \cdot \hat{\beta})\beta_j$$

where $\vec{\alpha}_j$ are the baseline and/or previous demodulation coefficient vectors.

To test crosstalk for the $j^{th}$ channel, compute $$\xi_k = \sum_{\ell=1}^{2\cdot order} \varsigma_{k,\ell}\hat{\alpha}_\ell$$

(where $\hat{\alpha}$ corresponds to the $j^{th}$ channel)
if $k \leq 2\cdot\text{order}$ then:
when the $j^{th}$ channel is on:

$$\text{crosstalk}_{k \neq j} = 20\ \log\left(\frac{\xi_k}{\xi_j}\right)$$

when the $j^{th}$ is channel off $$\text{crosstalk}_{k \neq j + 2\cdot order} = 20\ \log\left(\frac{\xi_{k+2\cdot order}}{\xi_{j+2\cdot order}}\right)$$

The example above uses 8 sources by way of example and not by way of limitation. One of ordinary skill in the art will further recognize that other combinations and activation patterns can be used as well. For example, in one embodiment calibration measurements are obtained using activation patterns sources (LEDs) when less than half of the sources are activated, and calibration measurements are obtained using combinations when more than half of the sources are activated. With N sources, up to $2^N$ different combinations of activation patterns are possible using the N sources. Thus, one of ordinary skill in the art will recognize that in various embodiments, the demodulation coefficients can be calculated using calibration data from many different activation patterns of activated and deactivated sources. Further, in the above example, the number of channels was equal to 2 times the order. One of ordinary skill in the art will recognize that the above analysis can also be used whenever number of channels is less than or equal to 2×order.

Although described above in connection with a particular embodiment of the present invention, it should be understood the description of the embodiment is illustrative of the invention and are not intended to be limiting. Although described above in connection with a pulse oximetry system wherein a parameter to be measured is the attenuation of red and infrared light passing through a portion of a subject's body, it should be understood that the method and apparatus described herein can also be used for other measurements where two or more signals are passed through a system to be analyzed. In particular, the present invention can be used to demodulate two combined parametric signals responsive to the system to be analyzed where the two parametric signals have a predetermined timing relationship between them, as described herein. The invention can be used in connection with various physiological parameter measurement systems, such as, for example, systems that measure blood constituents, blood oxygen carboxyhemoglobin, methemoglobin, glucose, etc. Various modifications and applications may occur to those skilled in the art without departing from the true spirit and scope of the invention as defined in the appended claims.

What is claimed is:

1. An apparatus for measuring one or more blood constituents in a subject, said apparatus comprising:
    a first signal source which applies a first input signal during a first time interval;
    a second signal source which applies a second input signal during a second time interval;
    a third signal source which applies a third input signal during a third time interval;
    a detector which detects a first signal responsive to said first input signal passing through a portion of said subject having blood therein, a second signal responsive to said second input signal passing through said portion of said subject, and a third signal responsive to said third input signal passing through a portion of said subject having blood therein, said detector generating a detector output signal responsive to said first, second, and third signals; and
    a signal processor which receives said detector output signal, said signal processor configured to demodulate said detector output signal by applying a first demodulation signal to a signal responsive to said detector output signal to generate a first demodulator output signal, applying a second demodulation signal to said signal responsive to said detector output signal to generate a second demodulator output signal, and applying a third demodulation signal to said signal responsive to said detector output signal to generate a third demodulator output signal, said signal processor configured to select said first demodulation signal, said second demodulation signal and said third demodulation signal to reduce crosstalk between said first, second, and third demodulator signals using, at least in part, first and second calibration data, wherein, to obtain the second calibration data, said first signal source, said second signal source, and said third signal source are operated in pairs such that for a time interval each of pairs of signal sources are operated alternatingly one at a time.

2. An apparatus for measuring one or more blood constituents in a subject, said apparatus comprising:
    a first signal source which applies a first input signal during a first time interval;
    a second signal source which applies a second input signal during a second time interval;
    a third signal source which applies a third input signal during a third time interval;
    a detector which detects a first signal responsive to said first input signal passing through a portion of said subject having blood therein and which detects a second signal responsive to said second input signal passing through said portion of said subject, and a third signal responsive to said third input signal, said detector generating a detector output signal responsive to said first, second, and third signals; and
    a signal processor which receives said detector output signal, said signal processor demodulating said detector output signal by applying a demodulation signal determined at least in part from a first dataset wherein each of said first, second, and third sources are activated one at a time and a second dataset wherein each of said first, second, and third sources are deactivated one at a time.

3. The apparatus of claim 2, wherein at least a portion of said first dataset comprises turning off only one of said first, second, or third signal sources and measuring between one of parametric signals and non-corresponding output signals.

4. The apparatus of claim 2, further comprising a fourth signal source and wherein at least a portion of said first dataset comprises a set of unique activation patterns wherein a plurality of said sources are active and a plurality of said sources are not active in each pattern.

5. The apparatus of claim 2, further comprising a fourth signal source and a fifth signal source and wherein at least a portion of said first dataset is obtained using a set of activation patterns wherein a plurality of said sources are active and a plurality of said sources are not active in each pattern and where each activation pattern is different.

* * * * *

UNITED STATES PATENT AND TRADEMARK OFFICE
CERTIFICATE OF CORRECTION

PATENT NO. : 12,171,552 B2
APPLICATION NO. : 18/309187
DATED : December 24, 2024
INVENTOR(S) : Walter M. Weber Page 1 of 2

It is certified that error appears in the above-identified patent and that said Letters Patent is hereby corrected as shown below:

On the Title Page

Column 2, Page 2 (U.S. Patent Documents), Line 78, delete "Ai-Ali" and insert -- Al-Ali --.

Column 1, Page 3 (U.S. Patent Documents), Line 12, delete "Ai-Ali" and insert -- Al-Ali --.

Column 1, Page 3 (U.S. Patent Documents), Line 70, delete "Ai-Ali" and insert -- Al-Ali --.

In the Specification

Column 8, Line 50, delete "$\hat{n}_K$," and insert -- $\hat{n}_K$ --.

Column 8, Line 59, delete "period T which" and insert -- period τ which --.

Column 9, Line 14, delete "through SM, where" and insert -- through $S_M$, where --.

Column 9, Line 37, delete "signals $S_t(t)$ are" and insert -- signals $S_i(t)$ are --.

Column 9, Line 39, delete "signals $M_t(t)$ and" and insert -- signals $M_i(t)$ and --.

Column 12, Line nos. 56-58 (approx.), delete "$\begin{bmatrix} S_1(t-\Delta) \\ S_2(t-\Delta) \end{bmatrix} = \begin{bmatrix} \cos\omega\Delta & -\sin\omega\Delta \\ \sin\omega\Delta & \cos\omega\Delta \end{bmatrix} LP \begin{bmatrix} D_1(t)S(t) \\ D_2(t)S(t) \end{bmatrix}$" and insert -- $\begin{bmatrix} S_1(t-\Delta) \\ S_2(t-\Delta) \end{bmatrix} = \begin{bmatrix} \cos\omega\Delta & \sin\omega\Delta \\ -\sin\omega\Delta & \cos\omega\Delta \end{bmatrix} \cdot LP \begin{bmatrix} D_1(t)S(t) \\ D_2(t)S(t) \end{bmatrix}$ --.

Column 12, Line nos. 60-61, delete "$= \left[\begin{bmatrix} \cos\omega\Delta & \sin\omega\Delta \\ -\sin\omega\Delta & \cos\omega\Delta \end{bmatrix} \begin{bmatrix} D_1(t) \\ D_2(t) \end{bmatrix}\right] S(t)$" and insert Signed and Sealed this
Fifteenth Day of April, 2025

Coke Morgan Stewart
*Acting Director of the United States Patent and Trademark Office*

CERTIFICATE OF CORRECTION (continued)
U.S. Pat. No. 12,171,552 B2

Column 12, Line nos. 62-63, delete "$= \begin{bmatrix} \begin{bmatrix} D_1(t) \\ D_2(t) \end{bmatrix} S(t) \end{bmatrix}$" and insert -- $= LP \begin{bmatrix} \begin{bmatrix} \bar{D}_1(t) \\ \bar{D}_2(t) \end{bmatrix} S(t) \end{bmatrix}$ --.

where the preceding expression is $= LP \begin{bmatrix} \begin{bmatrix} \cos\omega\Delta & \sin\omega\Delta \\ -\sin\omega\Delta & \cos\omega\Delta \end{bmatrix} \begin{bmatrix} D_1(t) \\ D_2(t) \end{bmatrix} S(t) \end{bmatrix}$ Column 13, Line 30, delete "$S_1(t)=A_1 S_1(t)\cos \phi_1 - A_2 S_2(t)\sin \phi_2$" and insert -- $\hat{S}_1(t) = A_1 S_1(t)\cos\phi_1 - A_2 S_2(t)\sin\phi_2$ --.

Column 15, Line 28 (approx.), delete "$\bar{D}_1(t)=\alpha_{11}\sin \omega t + \bar{\alpha}_{12}\cos \omega t$" and insert -- $\bar{D}_1(t) = \bar{\alpha}_{11}\sin\omega t + \bar{\alpha}_{12}\cos\omega t$ --.

Column 15, Line 47 (approx.), delete "and Tis a" and insert -- and T is a --.

Column 16, Line nos. 16-18 (approx.), delete "$\beta_0 = \frac{\gamma}{\left[\sum_k \gamma_{ik}^2\right]^{1/2}}$ where" and insert -- $\beta_{ij} = \frac{\gamma_{ij}}{\left[\sum_k \gamma_{ik}^2\right]^{1/2}}$ --.

Column 16, Line 22 (approx.), delete "Then $\bar{\alpha}_{11}\bar{\beta}_{11} + \bar{\alpha}_{12}\bar{\beta}_{12} = 0$" and insert -- $\bar{\alpha}_{11}\beta_{11} + \bar{\alpha}_{12}\beta_{12} = 0$ --.

Column 16, Line 23 (approx.), delete "$\bar{\alpha}_{21}\bar{\beta}_{21} + \bar{\alpha}_{22}\bar{\beta}_{22} = 0$" and insert -- $\bar{\alpha}_{21}\beta_{21} + \bar{\alpha}_{22}\beta_{22} = 0$ --.

Column 16, Line 29 (approx.), delete "$\bar{\alpha}_{ij}$" and insert -- $\alpha_{ij}$ --.

Column 18, Line 1, delete "and for i=2 order–1." and insert -- and for $i = 2 \cdot order - 1$, --.

Column 18, Line 18 (approx.), delete "$\hat{\alpha}_j = (\vec{\alpha}_j \cdot \hat{\beta})\beta_j$" and insert -- $\hat{\alpha}_j = (\vec{\alpha}_j \cdot \hat{\beta})\hat{\beta}_j$ --.